US011898182B2

(12) United States Patent
Cao et al.

(10) Patent No.: US 11,898,182 B2
(45) Date of Patent: Feb. 13, 2024

(54) METHOD FOR PREPARING R-HYDROXYNITRILE LYASE AND USE THEREOF

(71) Applicant: JIANGXI KEYUAN BIOPHARM CO., LTD., Jiujiang (CN)

(72) Inventors: Jinhui Cao, Jiujiang (CN); Kuang Zong, Jiujiang (CN); Hailiang Yu, Jiujiang (CN); Peng Zeng, Jiujiang (CN); Jianming Liu, Jiujiang (CN); Wenhuan Chen, Jiujiang (CN)

(73) Assignee: JIANGXI KEYUAN BIOPHARM CO., LTD., Jiujiang (CN)

( * ) Notice: Subject to any disclaimer, the term of this patent is extended or adjusted under 35 U.S.C. 154(b) by 0 days.

(21) Appl. No.: 17/815,447

(22) Filed: Jul. 27, 2022

(65) Prior Publication Data

US 2023/0072514 A1 Mar. 9, 2023

(30) Foreign Application Priority Data

Aug. 26, 2021 (CN) ......................... 202110985869.6

(51) Int. Cl.
*C12N 9/88* (2006.01)
*C12N 1/20* (2006.01)
*C12N 15/52* (2006.01)
*C12P 13/00* (2006.01)

(52) U.S. Cl.
CPC ................. *C12N 9/88* (2013.01); *C12N 1/20* (2013.01); *C12N 15/52* (2013.01); *C12P 13/004* (2013.01); *C12Y 401/02046* (2013.01)

(58) Field of Classification Search
CPC .. C12N 9/88; C12N 1/20; C12N 15/52; C12P 13/004; C12Y 401/02046
See application file for complete search history.

(56) References Cited

PUBLICATIONS

Snapgene, An overview of the science behind cloning with restriction enzymes and how to simulate restriction cloning in SnapGene (Year: 2023).*
Genscript, In-Frame—Your Open Reading Guide Molecular Cloning: Restriction Cloning Troubleshooting & Tips (Year: 2018).*
Appendix A, Restriction site map of SEQ ID No. 1 (Year: 2023).*
Appendix B, Restriction site map of SEQ ID No. 2 (Year: 2023).*

* cited by examiner

*Primary Examiner* — Thomas J. Visone
*Assistant Examiner* — Mary A Crum
(74) *Attorney, Agent, or Firm* — Pearne & Gordon LLP

(57) ABSTRACT

Methods for synthesizing and using R-hydroxynitrile lyase derived from mango. Specifically, a variety of mutant cyanohydrin lyases were obtained by mutating a wild-type hydroxynitrile lyase gene, adding an enzyme cleavage site thereto, preparing a recombinant plasmid by inserting the mutated wild-type hydroxynitrile lyase gene into a vector, introducing the recombinant plasmid into a strain of bacteria, and secreting and expressing the R-hydroxynitrile lyase in the strain. The method Is safe, simple and easy to operate.

4 Claims, No Drawings

Specification includes a Sequence Listing.

METHOD FOR PREPARING R-HYDROXYNITRILE LYASE AND USE THEREOF

CROSS REFERENCE TO RELATED APPLICATION

This patent application claims the benefit and priority of Chinese Patent Application No. 202110985869.6 filed with the China National Intellectual Property Administration on Aug. 26, 2021, the disclosure of which is incorporated by reference herein in its entirety as part of the present application.

SEQUENCE LISTING

The material in the XML text file, named HLP20220400882.xml, created Jul. 7, 2022, file size of 10,749 bytes, is hereby incorporated by reference.

TECHNICAL FIELD

The present disclosure relates to the technical field of biotechnology, in particular to a method for preparation and use of R-hydroxynitrile lyase.

BACKGROUND

Chiral cyanoalcohols (ester) are a type of chiral raw material that plays an important role in industrial asymmetric synthesis and production. At the same time, it can be easily converted into commercially valuable pharmaceutical and pesticide intermediates such as chiral α-hydroxy acid (ester), α-amino acid, β-amino alcohols. Therefore, the synthesis of chiral cyanoalcohols has always been one of the hotspots in academical and industrial fields. The synthesis of chiral cyanoalcohol is tough and challenging, and its asymmetric synthesis requires the use of chiral chemistry or biocatalysts. Among them, biocatalysts (hydroxynitrile lyase) are far superior to chemical catalysts and are widely used in the organic synthesis industry due to their availability, low cost, high catalytic efficiency, mild reaction conditions, and high yield. It has the characteristics of high efficiency and optical purity, and a wide range of substrates.

Cyanoalcohol (lyase) enzymes catalyze the addition of HCN to aldehydes and ketones to produce α-chiral cyanohydrin product. Naturally occurring R-hydroxynitrile lyase exists in *Rosaceae prunus* plants and some fruits. Presently, only those R-hydroxynitrile lyase derived from Rosaceae plants are successful cases of industrial application, such as *Prunus amygdalus* (Pa HNL), *Prunus domestica* (Pd HNL) or *Prunus mume* (PmHNL), etc., among which the hydroxynitrile lyase of *Prunus amygdalus* (Pa HNL) is the major one, so it is of great practical significance to find hydroxynitrile lyase from other sources and cast it in industrial production of chiral cyanoalcohol.

SUMMARY

This section is to outline some aspects of embodiments of the present disclosure and to briefly introduce some preferred embodiments. Some simplifications or omissions may be made in this section and the abstract and title of the application to avoid obscuring the purpose of this section, abstract and title, and such simplifications or omissions may not be used to limit the scope of the present disclosure.

In view of the above-mentioned and/or existing problems in the existing preparation method of R-hydroxynitrile lyase, the present disclosure is thus proposed.

Therefore, one of the objectives of the present disclosure is to provide a preparation method and use of R-hydroxynitrile lyase.

According to one aspect of the present disclosure, the present disclosure provides the following technical scheme to solve the above-mentioned technical problems: a method for preparing R-hydroxynitrile lyase, comprising the following steps:

mutating R-hydroxynitrile lyase wild-type gene, comprising: mutating a wild-type gene sequence of R-hydroxynitrile lyase set forth in SEQ ID NO. 1 to obtain a hydroxynitrile lyase mutant gene having a gene sequence set forth in SEQ ID NO. 2;

adding an enzyme cleavage site, comprising: inserting a double digestion site into the hydroxynitrile lyase mutant gene;

preparing a recombinant plasmid, comprising: inserting hydroxynitrile lyase mutant gene into an expression vector to obtain a recombinant plasmid;

introducing a strain, comprising: introducing the recombinant plasmid with the hydroxynitrile lyase mutant gene into the a strain to obtain a recombinant expression strain;

performing secretion and expression of the strain, comprising: inducing the recombinant expression strain to express an enzyme in a culture medium and collecting the enzyme liquid.

In a preferred embodiment of the method for preparing R-hydroxynitrile lyase in the present disclosure, the mutating is conducted by using error-prone PCR.

In a preferred embodiment of the method for preparing R-hydroxynitrile lyase in the present disclosure, the double digestion site is NdeI/HindIII in the step of adding an enzyme cleavage site.

In a preferred embodiment of the method for preparing R-hydroxynitrile lyase in the present disclosure, the expression vector is pET26b(+) which contains a signal peptide pelB leaderAs a preferred embodiment of the method for preparing R-hydroxynitrile lyase in the present disclosure at N-terminal in the step of preparing the recombinant plasmid.

In a preferred embodiment of the method for preparing R-hydroxynitrile lyase in the present disclosure, wherein in the step of introducing a strain, the stain is *E. coli* BL21 (DE3).

In a preferred embodiment of the method for preparing R-hydroxynitrile lyase in the present disclosure, wherein in the step of performing secretion and expression of the strain, the culture medium is LB culture medium.

In a preferred embodiment of the method for preparing R-hydroxynitrile lyase in the present disclosure, the method further comprises a step of performing induction culturing in the step of performing secretion and expression of the strain also include induction culture, and when OD600 of the culture medium=1.0, 0.2 mM IPTG is added and the temperature was kept at 30° C., and the expression is induced for 4-5 h.

The present disclosure also discloses use of product obtained by the method for preparing R-hydroxynitrile lyase of the present disclosure, wherein the use comprises steps of:

dissolving a substrate in methyl tert-butyl ether (MTBE) to obtain an MTBE solution of the substrate; diluting the obtained product by the present method in a phosphate-citric acid buffer, and adjusting pH to 3.4 to obtain an enzyme solution; mixing thoroughly the MTBE solution of the substrate and the enzyme solution, lowering temperature of the system to 10° C., and stirring the system to form an emulsion, and adding liquid hydrogen cyanide for reaction to obtain R-phenylethyl cyanohydrin and R-o-methyl phenylethyl cyanohydrin.

In the use of the product obtained by the method for preparing R-hydroxynitrile lyase in the present disclosure, the substrate is one or two of phenylethyl cyanohydrin and o-methyl phenylethyl cyanohydrin; concentration of the MTBE solution is 8 microliters per milliliter of buffer solution; volume ratio of the MTBE solution of the substrate to the enzyme solution is 2:1.2-1.7; and ratio of addition amount of the liquid hydrogen cyanide to total volume of the MTBE solution of the substrate and the enzyme solution is 4-3.5:1.2.

The present disclosure further provide a product obtained by the method for preparing R-hydroxynitrile lyase in the present disclosure, wherein the product has a yield of ≥99.5% both for R-phenylethyl cyanohydrin and R-o-methyl phenylethyl cyanohydrin, and the chirality value (ee value) are both ≥99.5%.

Beneficial effects of the present disclosure:

The present disclosure provides a new method for preparing and use of R-hydroxynitrile lyase derived from mango. Particularly, by constructing random mutation and site-saturation mutagenesis libraries, and using a variety of mutant hydroxynitrile lyases through high-throughput screening, both R-phenylethyl cyanohydrin and R-o-methyl phenylethyl cyanohydrin are synthesized in a yield ≥99.5%, and the chirality value (ee value) is ≥99.5%. The method is safe, simple and easy to operate.

DETAILED DESCRIPTION OF THE EMBODIMENTS

In order to make the above objectives, features and advantages of the present disclosure more apparent and easy to understand, the specific embodiments of the present disclosure will be described in detail below with reference to the embodiments of the present disclosure.

In the following description, many specific details are set forth to facilitate a full understanding of the present disclosure, but the present disclosure can also be implemented in other ways different from those described herein, and those skilled in the art can make such modifications without departing from the connotation of the present disclosure. Therefore, the present disclosure is not limited by the specific embodiments disclosed below.

Moreover, reference herein to “one embodiment” or “an embodiment” refers to a particular feature, structure, or characteristic that may be included in at least one implementation mode of the present disclosure. The appearances of “in one embodiment” in various places in this specification are not intend to refer to the same embodiment, nor are they separate or selectively mutually exclusive from other embodiments.

In the examples of the present disclosure, R-selective hydroxynitrile lyase derived from mango (*Mangifera indica*) was used.

Both methyl tert-butyl ether and liquid hydrocyanic acid used in the present disclosure were of analytical grade, and other raw materials and reagents were commercially available unless otherwise specified.

Example 1

The specific principle for the design of the present disclosure is to obtain a variety of mutant hydroxynitrile lyase by constructing random mutation and site-saturation mutagenesis libraries and high-throughput screening.

The source of the R-hydroxynitrile lyase mutant is wild-type hydroxynitrile lyase. The specific synthesis method was as follows: restriction sites NdeI and HindIII were added to the hydroxynitrile lyase wild gene set forth in SEQ ID NO. 1 or the hydroxynitrile lyase mutant gene set forth in SEQ ID NO. 2, and inserted into the expression vector pET26b (+) after DNA digestion to obtain a recombinant plasmid, and the recombinant plasmid was transformed into *E. coli* BL21(DE3) to construct a recombinant expression strain. After the above recombinant strains were cultured in LB culture medium to OD600=1.0, 0.2 mM IPTG was added and cultured at 30° C. for 4 to 5 hours. The wild-type or mutant cells were collected by centrifugation, and the crude enzyme solution was obtained after the cells were lysed by sonication.

Example 2

The method for preparing wild-type hydroxynitrile lyase mutant was conducted as follows.

The hydroxynitrile lyase wild-type gene sequence of mango (*Mangifera indica*) is set forth in SEQ ID NO. 1, and the random mutations were introduced by error-prone PCR and/or the site-saturation mutagenesis was introduced based on docking between the enzyme protein structure and the mimetic substrate. Then high-throughput screening was performed to obtain the wild-type mutant of hydroxynitrile lyase of the present disclosure, which had a sequence set forth in SEQ ID NO. 2.

The protein sequence of the wild-type hydroxynitrile lyase of mango (*Mangifera indica*) after transcription and translation is shown in SEQ ID NO. 3. The protein sequence of the wild-type hydroxynitrile lyase mutant is shown in SEQ ID NO. 4. Compared with the wild-type hydroxynitrile lyase, the wild-type hydroxynitrile lyase mutant had the difference lied in that isoleucine at position 109 was mutated to methionine, asparagine at position 110 was mutated to alanine or serine, and isoleucine at position 321 was mutated to threonine or alanine, proline at position 354 was mutated to isoleucine, and serine at position 355 was mutated to leucine. The sequence (SEQ ID NO. 4) indicated a possible protein sequence. However, other protein sequences that were possibly mutated had the same property.

Except for the sequence as shown in SEQ ID No.2, there was a possibility that the residues of R-hydroxynitrile lyase mutant gene at positions 325-327 were altered to ATG, residues at positions 328-330 were altered to GCT or AGT, residues at positions 961-963 were altered to ACT or GCT, residues at positions 1060-1062 were altered to ATA, and residues at positions 1063-1065 were altered to TTA or TTG. There were also included any case where alterations occurred at any above-mentioned sites.

Example 3

The steps of hydroxynitrile lyase high-throughput screening were conducted as follows: 130 μL of 100 mM potassium phosphate-citric acid buffer (pH=5.0), 20 μL of diluted hydroxynitrile lyase solution were added to the 96-well plate in sequence at 25° C., and finally 50 μL of the substrate solution of phenylethyl cyanohydrin or o-methyl phenylethyl cyanohydrin was added. Change in absorbance at 280 nm within 5 minutes was read using a microplate reader, and the change in absorbance represented the level of enzyme activity.

Substrate solution: 100 mM pH=3.5 potassium phosphate-citric acid buffer was used to prepare a buffer having a concentration of 8 microliters per milliliter of buffer.

Example 4

Application of R-hydroxynitrile lyase: R-hydroxynitrile lyase was used in a method for synthesizing R-phenylethyl cyanohydrin and R-o-methyl phenylethyl cyanohydrin. And the method was conducted as follows.

15 mmol of substrate was dissolved in 2.1 mL of methyl tert-butyl ether (MTBE) to obtain a MTBE solution of the substrate. The resulting hydroxynitrile lyase was diluted in 10 mM phosphate-citrate buffer to make a total volume of 3.7 mL, and the pH was adjusted to 3.4. The MTBE solution of the substrate and the enzyme solution were fully mixed, and the temperature of the system was lowered to 10° C. After stirring, an emulsion was formed, and 1.2 ml of liquid hydrocyanic acid was added to start the reaction.

Sampling were conducted at different time points, a column was derivatized with acetic anhydride in the presence of pyridine and dichloromethane, and analyzed by GC on a cyclodextrin column (CP-Chirasil-Dex CB) to determine the substrate conversion and enantiomers value.

After the conversion of the substrate was completed, MTBE was added in 1 volume of the aqueous phase, extracted three times, the organic phases were combined and dehydrated with anhydrous sodium sulfate, and then concentrated under reduced pressure to obtain the product. Table 1 shows the relationship between the product yield, product chirality value and the amount of hydroxynitrile lyase added when 15 mmol of substrate was added.

TABLE 1

Relationship between product yield, product chirality value and the amount of hydroxynitrile lyase added

| Substrate name | Addition amount of cyanohydrin (mg) | Product yield (%) | Product chirality value (e.e) |
|---|---|---|---|
| phenylethyl cyanohydrin | 0 | 92.33 | 75.32 |
| phenylethyl cyanohydrin | 1.5 | 99.55 | 99.63 |
| phenylethyl cyanohydrin | 3.0 | 99.87 | 99.92 |
| o-methyl phenylethyl cyanohydrin | 0 | 91.08 | 84.77 |
| o-methyl phenylethyl cyanohydrin | 1.5 | 99.77 | 99.57 |
| o-methyl phenylethyl cyanohydrin | 3.0 | 99.82 | 99.79 |

It can be concluded from Table 1 that both of the yields of the synthesized R-phenylethyl cyanohydrin and R-o-methyl phenylethyl cyanohydrin were ≥99.5%, and the chirality values (ee values) are both ≥99.5%.

The present disclosure provides a new method for preparing and use of R-hydroxynitrile lyase derived from mango. Particularly, the present disclosure provides a method in which a variety of mutant hydroxynitrile lyase are obtained through the construction of random mutation and site-saturation mutagenesis libraries, as well as high-throughput screening, the method is safe, simple and easy to operate.

It should be noted that the above embodiments are merely used to describe the technical solutions of the present disclosure and not intend to limit technical solutions of the present disclosure. Although the present disclosure has been described in detail with reference to the preferred embodiments, those of ordinary skill in the art should understand that modifications or equivalent substitutions of the technical solutions of the present disclosure can be made without departing from the spirit and scope of the technical solutions of the present disclosure, and those modifications or equivalent substitutions should be deem as falling within the scope of the claims of the present disclosure.

What is claimed is:

1. A method for preparing R-hydroxynitrile lyase, comprising:

mutating R-hydroxynitrile lyase wild-type gene, comprising: mutating the wild-type gene sequence of R-hydroxynitrile lyase set forth in SEQ ID NO. 1 to obtain a hydroxynitrile lyase mutant gene having the gene sequence set forth in SEQ ID NO. 2, wherein:

bases ATC at positions 325-327 of SEQ ID NO. 1 are substituted for bases ATG, bases AAT at positions 328-330 of SEQ ID NO. 1 are substituted for bases AGT, bases ATT at positions 961-963 of SEQ ID NO. 1 are substituted for bases ACT, bases CCA at positions 1060-1062 of SEQ ID NO. 1 are substituted for bases ATA, and bases TCT at positions 1063-1065 of SEQ ID NO. 1 are substituted for bases TTA;

adding an enzyme cleavage site, comprising: adding a double digestion site to the hydroxynitrile lyase mutant gene, wherein the double digestion site is Ndel/Hindllll;

preparing a recombinant plasmid, comprising: inserting the hydroxynitrile lyase mutant gene into an expression vector to obtain a recombinant plasmid, wherein the expression vector is pET26b(+), N-terminus of the expression vector is a signal peptide pelB leader having the gene sequence set forth in SEQ ID NO. 5;

introducing the recombinant plasmid into a strain, comprising: introducing the recombinant plasmid with the hydroxynitrile lyase mutant gene into the strain to obtain a recombinant expression strain, wherein the strain is *E. coli* BL21 (DE3); and expressing and secreting the R-hydroxynitrile lyase in the strain, comprising: culturing the recombinant expression strain, and inducing the recombinant expression strain to express the enzyme of R-hydroxynitrile lyase in a culture medium and collecting a resulting enzyme liquid.

2. The method according to claim 1, wherein the mutating is conducted by error-prone PCR.

3. The method according to claim 1, wherein the culture medium is LB culture medium.

4. The method according to claim 1, wherein the method further comprises a step of performing induction culturing when expressing and secreting the R-hydroxynitrile lyase in the strain, comprising adding 0.2 mM IPTG to the culture medium when OD600 of the culture medium is 1.0, keeping a culture temperature at 30° C., and inducing expression for 4-5 hours.

* * * * *

SEQUENCE LISTING

```
Sequence total quantity: 5
SEQ ID NO: 1            moltype = DNA  length = 1614
FEATURE                 Location/Qualifiers
source                  1..1614
                        mol_type = other DNA
                        organism = Mangifera indica
SEQUENCE: 1
caaatatttt tctttacatc agaaccaagt tacatgaagt ttgtgtataa tgccacggac  60
tttccatcag aggactacta tgactacatt attgtaggag gaggcactgc ggggagtcca  120
ttagcggcaa cactctcaga atcttttaaa gtacttgttt tggaacgtgg tggtgtgcct  180
tatggcaaac gcaatttgat gactcaagaa gggttcttgg ccaccctctt ggacgttgat  240
acttatgatt ctcctgctca agccttcaga tctgaggaag gagttccaaa tgctcgaggc  300
cgtgttcttg gtggaagtag tgccatcaat gctgggtttt atagccgggc agatcaagat  360
ttctatcaga aatcaggtat gcattgggac cttagagttg ttaatgagtc ttatgagtgg  420
gtagagaagc tggttgtgtt taggcctgag ttgagaggtt ggcaatctgc tgttagagat  480
gggttgttgg aggctggtgt tgatccttat aatgggttta atttgaatca tgttttgggg  540
actaagattg gtggttcaac ttttgatagt tcaggtaggc ggcatagtgc tgctgacctt  600
cttagttatg cagaaggttc gaatattaga gttgctgttt atgcaagtgt ggagaggatt  660
ttgttggcat cttcttcagc tgattctggg gctaaacaga cagcaattgg tgtggtttat  720
cgtgatgcaa ttgggcggta tcatcatgca atgttgaggg aaaatggtga agtgatggta  780
tgtgctggtg ctattgggag tccgcagttg ttgttgttga gtggcattgg tccaaggcct  840
tatctatcaa cttgggggat tccagtggca tttcataatc catatgttgg gcagtacctt  900
```

-continued

```
tatgataatc caaggaatgg tatatcaatt gtgcctccaa tcccactaga tcactcattg  960
attcaggttg ttggcattac tgaattaggg gcttatgttg aagcagcctc caatgttatt  1020
ccttttgcat ccccagctcg gtctattttc atcgggacac catcttcgcc tctttacgta  1080
actgtggcta ccctcatgga gaagattatt gggccagttt caagtggtac attaaggctg  1140
gcttcaaccg acatcagggt gaatccaatt gttcggttta attacttcag caacccagtg  1200
gatattgaaa ggtgtatcaa tggcacacgc aagattggtg acattctaag gagccgatcc  1260
atggatattt tcaagttcag agattggttt ggtactagga atttcaggtt tgtagggcct  1320
gcattgcctg ttgatcaatc taaccatgcc caaatggcta atttctgtcg tcgtactgtt  1380
agcactatat ggcattacca tggaggctgt gttgtgggga aagtagtcga tggtgaacac  1440
cgtgtacttg gcatcgatgc tctccgaatt gttgatggat caacgtttaa aatatcacca  1500
ggaaccaacc ctcaggctac cttgatgatg cttggaagat atgttggatt gaagattcta  1560
aaagagcgat caatccggtt ggaggctatt cataatattc aagagtccat gtga        1614

SEQ ID NO: 2           moltype = DNA  length = 1614
FEATURE                Location/Qualifiers
misc_feature           1..1614
                       note = sequence of hydroxynitrile lyase mutant gene
source                 1..1614
                       mol_type = other DNA
                       organism = synthetic construct
SEQUENCE: 2
caaatatttt tctttacatc agaaccaagt tacatgaagt ttgtgtataa tgccacggac  60
tttccatcag aggactacta tgactacatt attgtaggag gaggcactgc ggggagtcca  120
ttagcggcaa cactctcaga atcttttaaa gtacttgttt tggaacgtgg tggtgtgcct  180
tatggcaaac gcaatttgat gactcaagaa gggttcttgg ccaccctctt ggacgttgat  240
acttatgatt ctcctgctca agccttcaga tctgaggaag gagttccaaa tgctcgaggc  300
cgtgttcttg gtggaagtag tgccatgagt gctgggtttt atagccgggc agatcaagat  360
ttctatcaga aatcaggtat gcattgggac cttagagttg ttaatgagtc ttatgagtgg  420
gtagagaagc tggttgtgtt taggcctgag ttgagaggtt ggcaatctgc tgttagagat  480
gggttgttgg aggctggtgt tgatccttat aatgggttta atttgaatca tgttttgggg  540
actaagattg gtggttcaac ttttgatagt tcaggtaggc ggcatagtgc tgctgacctt  600
cttagttatg cagaaggttc gaatattaga gttgctgttt atgcaagtgt ggagaggatt  660
ttgttggcat cttcttcagc tgattctggg gctaaacaga cagcaattgg tgtggtttat  720
cgtgatgcaa ttgggcggta tcatcatgca atgttgaggg aaaatggtga agtgatggta  780
tgtgctggtg ctattgggag tccgcagttg ttgttgttga gtggcattgg tccaaggcct  840
tatctatcaa cttgggggat tccagtggca tttcataatc catatgttgg gcagtacctt  900
tatgataatc caaggaatgg tatatcaatt gtgcctccaa tcccactaga tcactcattg  960
actcaggttg ttggcattac tgaattaggg gcttatgttg aagcagcctc caatgttatt  1020
ccttttgcat ccccagctcg gtctattttc atcgggacaa tattatcgcc tctttacgta  1080
actgtggcta ccctcatgga gaagattatt gggccagttt caagtggtac attaaggctg  1140
gcttcaaccg acatcagggt gaatccaatt gttcggttta attacttcag caacccagtg  1200
gatattgaaa ggtgtatcaa tggcacacgc aagattggtg acattctaag gagccgatcc  1260
atggatattt tcaagttcag agattggttt ggtactagga atttcaggtt tgtagggcct  1320
gcattgcctg ttgatcaatc taaccatgcc caaatggcta atttctgtcg tcgtactgtt  1380
agcactatat ggcattacca tggaggctgt gttgtgggga aagtagtcga tggtgaacac  1440
cgtgtacttg gcatcgatgc tctccgaatt gttgatggat caacgtttaa aatatcacca  1500
ggaaccaacc ctcaggctac cttgatgatg cttggaagat atgttggatt gaagattcta  1560
aaagagcgat caatccggtt ggaggctatt cataatattc aagagtccat gtga        1614

SEQ ID NO: 3           moltype = AA  length = 537
FEATURE                Location/Qualifiers
source                 1..537
                       mol_type = protein
                       organism = Mangifera indica
SEQUENCE: 3
QIFFFTSEPS YMKFVYNATD FPSEDYYDYI IVGGGTAGSP LAATLSESFK VLVLERGGVP  60
YGKRNLMTQE GFLATLLDVD TYDSPAQAFR SEEGVPNARG RVLGGSSAIN AGFYSRADQD  120
FYQKSGMHWD LRVVNESYEW VEKLVVFRPE LRGWQSAVRD GLLEAGVDPY NGFNLNHVLG  180
TKIGGSTFDS SGRRHSAADL LSYAEGSNIR VAVYASVERI LLASSSADSG AKQTAIGVVY  240
RDAIGRYHHA MLRENGEVMV CAGAIGSPQL LLLSGIGPRP YLSTWGIPVA FHNPYVGQYL  300
YDNPRNGISI VPPIPLDHSL IQVVGITELG AYVEAASNVI PFASPARSIF IGTPSSPLYV  360
TVATLMEKII GPVSSGTLRL ASTDIRVNPI VRFNYFSNPV DIERCINGTR KIGDILRSRS  420
MDIFKFRDWF GTRNFRFVGP ALPVDQSNHA QMANFCRRTV STIWHYHGGC VVGKVVDGEH  480
RVLGIDALRI VDGSTFKISP GTNPQATLMM LGRYVGLKIL KERSIRLEAI HNIQESM     537

SEQ ID NO: 4           moltype = AA  length = 537
FEATURE                Location/Qualifiers
REGION                 1..537
                       note = protein sequence of wild-type hydroxynitrile lyase
                        mutant
source                 1..537
                       mol_type = protein
                       organism = synthetic construct
SEQUENCE: 4
QIFFFTSEPS YMKFVYNATD FPSEDYYDYI IVGGGTAGSP LAATLSESFK VLVLERGGVP  60
YGKRNLMTQE GFLATLLDVD TYDSPAQAFR SEEGVPNARG RVLGGSSAMS AGFYSRADQD  120
FYQKSGMHWD LRVVNESYEW VEKLVVFRPE LRGWQSAVRD GLLEAGVDPY NGFNLNHVLG  180
TKIGGSTFDS SGRRHSAADL LSYAEGSNIR VAVYASVERI LLASSSADSG AKQTAIGVVY  240
RDAIGRYHHA MLRENGEVMV CAGAIGSPQL LLLSGIGPRP YLSTWGIPVA FHNPYVGQYL  300
```

-continued

```
YDNPRNGISI VPPIPLDHSL AQVVGITELG AYVEAASNVI PFASPARSIF IGTILSPLYV  360
TVATLMEKII GPVSSGTLRL ASTDIRVNPI VRFNYFSNPV DIERCINGTR KIGDILRSRS  420
MDIFKFRDWF GTRNFRFVGP ALPVDQSNHA QMANFCRRTV STIWHYHGGC VVGKVVDGEH  480
RVLGIDALRI VDGSTFKISP GTNPQATLMM LGRYVGLKIL KERSIRLEAI HNIQESM     537

SEQ ID NO: 5            moltype = DNA  length = 66
FEATURE                 Location/Qualifiers
misc_feature            1..66
                        note = gene sequence of signal peptide
source                  1..66
                        mol_type = other DNA
                        organism = synthetic construct
SEQUENCE: 5
atgaaatacc tgctgccgac cgctgctgct ggtctgctgc tcctcgctgc ccagccggcg  60
atggcc                                                             66
```